US012629154B2

(12) United States Patent
Thibodeau et al.

(10) Patent No.: US 12,629,154 B2
(45) Date of Patent: May 19, 2026

(54) MULTI HELICAL BROACHING PUNCH FOR OSTEOTOMY CREATION

(71) Applicant: Conmed Corporation, Largo, FL (US)

(72) Inventors: Robert Thibodeau, Saint Petersburg, FL (US); Patrick Barton, Palm Harbor, FL (US)

(73) Assignee: Conmed Corporation, Largo, FL (US)

( * ) Notice: Subject to any disclaimer, the term of this patent is extended or adjusted under 35 U.S.C. 154(b) by 530 days.

(21) Appl. No.: 17/980,133

(22) Filed: Nov. 3, 2022

(65) Prior Publication Data

US 2023/0135038 A1     May 4, 2023

Related U.S. Application Data

(60) Provisional application No. 63/275,134, filed on Nov. 3, 2021.

(51) Int. Cl.
*A61B 17/16*          (2006.01)
(52) U.S. Cl.
CPC ...... *A61B 17/1615* (2013.01); *A61B 17/1655* (2013.01)
(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1655; A61B 17/1657; A61B 17/1659
See application file for complete search history.

(56) References Cited

U.S. PATENT DOCUMENTS

| | | | |
|---|---|---|---|
| 6,312,432 B1 * | 11/2001 | Leppelmeier ...... | A61B 17/1615 |
| | | | 408/230 |
| 7,632,273 B2 | 12/2009 | Schnieders et al. | |
| 7,749,225 B2 * | 7/2010 | Chappuis ........... | A61B 17/1617 |
| | | | 606/167 |
| 9,226,756 B2 | 1/2016 | Teisen et al. | |
| 9,408,599 B2 | 8/2016 | Kaiser et al. | |
| 9,687,252 B2 | 6/2017 | Kelman et al. | |
| 10,136,902 B2 * | 11/2018 | Farris ................ | A61B 17/1655 |
| 10,188,404 B2 | 1/2019 | Dees et al. | |
| 10,219,841 B1 | 3/2019 | Compton et al. | |
| 10,238,400 B2 * | 3/2019 | Larsen ................... | A61B 17/02 |
| 10,265,083 B2 | 4/2019 | Servidio et al. | |
| 10,271,862 B2 * | 4/2019 | Thomas ............. | A61B 17/1735 |
| 10,492,799 B2 | 12/2019 | Wolfson et al. | |
| 10,582,943 B2 | 3/2020 | Richter et al. | |
| 10,792,053 B2 | 10/2020 | Asfora et al. | |

(Continued)

*Primary Examiner* — Eric S Gibson
(74) *Attorney, Agent, or Firm* — Bond, Schoeneck & King, PLLC; Frederick J.M. Price

(57)                ABSTRACT

A broaching punch for creating osteotomies that has a tip with helical broaching features extending along the outer surface to a tip. The helical broaching features are each formed by an edge that extends outwardly from and around the body of the tip and characterized by a predetermined angle, depth, spacing, and arrangement of various dimensional combinations that slowly and progressively broaching more and more bone material away during insertion, thereby slowly growing the diameter of the osteotomy until it reaches the desired diameter. Tapping features may be included proximately to the broaching features to allow for a newly formed hole to be tapped with threads.

6 Claims, 7 Drawing Sheets

(56)          References Cited

U.S. PATENT DOCUMENTS

| | | | |
|---|---|---|---|
| 10,925,620 B2 | 2/2021 | Bowman et al. | |
| 10,925,621 B2 | 2/2021 | Flom et al. | |
| 11,039,842 B1 * | 6/2021 | Bennett ................ | A61B 17/164 |
| 11,324,493 B2 | 5/2022 | Dreyfuss et al. | |
| 2010/0324562 A1 * | 12/2010 | Thomsen ........... | A61B 17/1604 |
| | | | 606/80 |
| 2011/0238069 A1 * | 9/2011 | Zajac ................. | A61B 17/1655 |
| | | | 606/79 |
| 2012/0004661 A1 * | 1/2012 | Leppelmeier ...... | A61B 17/1615 |
| | | | 606/80 |
| 2017/0027592 A1 * | 2/2017 | Farris ................. | A61B 17/1615 |
| 2020/0113712 A1 | 4/2020 | Luna et al. | |
| 2021/0196285 A1 | 7/2021 | Hathaway et al. | |
| 2021/0251639 A1 | 8/2021 | Woodard et al. | |
| 2023/0135038 A1 * | 5/2023 | Thibodeau ......... | A61B 17/1604 |
| | | | 606/80 |

* cited by examiner

12

30

14

32

14-1    14-2/22                    14-1    14-2/22

14                         14

Angle 1        Angle 2        Angle 3

MULTI HELICAL BROACHING PUNCH FOR OSTEOTOMY CREATION

BACKGROUND

1. Field

The present application relates to an osteotomy punch and, more specifically, to a punch having multiple helixes.

2. Description of the Related Art

The creation of osteotomies is a common step for the insertion and function of many medical devices. Osteotomies may be used as pilot holes or as functional cavities to serve as an anchoring or fixation point, or even a void in which a medical device can reside and function. Traditional punches are osteodilators that create osteotomies by compressing and dilating the bone around the outside of the punch. Traditional punches are designed to reduce the force of insertion by having tapered distal ends and a featureless or smooth outer surface to reduce the friction during insertion because creating osteotomies via compression and dilation requires a large amount of force due to the biomechanical properties of bone that resist compression.

BRIEF SUMMARY

Traditional approaches to osteotomy punches cause a wide variety of problems. For example, large insertion forces can result in the cracking or fracturing of the bone during insertion, which causes unnecessary damage to the healthy tissue of the patient, increases healing time, and reduces the functional strength of a medical device inserted into the osteotomy. Higher insertion forces also increase the reaction force of the bone onto the punch, which can be seen and felt by the user, as the bone compresses back onto the punch making it very difficult to remove. As a result, users often have to strike the punch in the reverse direction, away from the patient, in order to remove the punch. Reaction forces can also cause the surrounding bone to expand back into the pilot hole when a traditional punch is removed, resulting in an osteotomy with a smaller diameter than the punch. This causes an issue with devices that require a specifically designed pilot hole and the dimensions of the osteotomy affect the functionality of the device.

As a result, the inventors recognize that there is a need for an osteotomy punch that relieves these problems by creating osteotomies by broaching instead of osteodilation. In various aspects, the structural designs herein reduce osteotomy insertion forces by slowly and progressively broaching more and more bone material away during insertion, thereby slowly growing the diameter of the osteotomy until it reaches the desired diameter. The various aspects of the structural designs also allow for removal by rotation and unscrewing from the bone which circumvents the reaction force of the bone and allows for easy removal by the user. The various structural aspects are thus more beneficial for the user (medical practitioner) and for the patient because they provide a more efficient means of creating an osteotomy that reduces the insertion force required to make the osteotomy, greatly reduce the chance of bone fracture due to insertion forces, and provide a much easier means of device removal. Embodiments described and illustrated herein work very at creating bone holes by taking small cuts of material to gradually bring the hole to the required size.

Furthermore, unlike a conventional drill bit—which cuts rotationally at its tip only while using flutes of the drill bit positioned proximally to the tip to assist with movement of chips created by the cutting away from the tip (per a particular tip configuration as should be understood by a person of ordinary skill in the art in conjunction with a review of this disclosure)—embodiments of the broaching punches described and illustrated herein are configured to punch and cut through bone axially when in use per a force directed axially in the direction of the distal point of the punch tip. Embodiments of the broaching punch are configured to do so per the broaching features, described and illustrated herein.

BRIEF DESCRIPTION OF THE SEVERAL VIEWS OF THE DRAWING(S)

The present disclosure will be more fully understood and appreciated by reading the following Detailed Description in conjunction with the accompanying drawings, in which.

DETAILED DESCRIPTION

Figure 1:
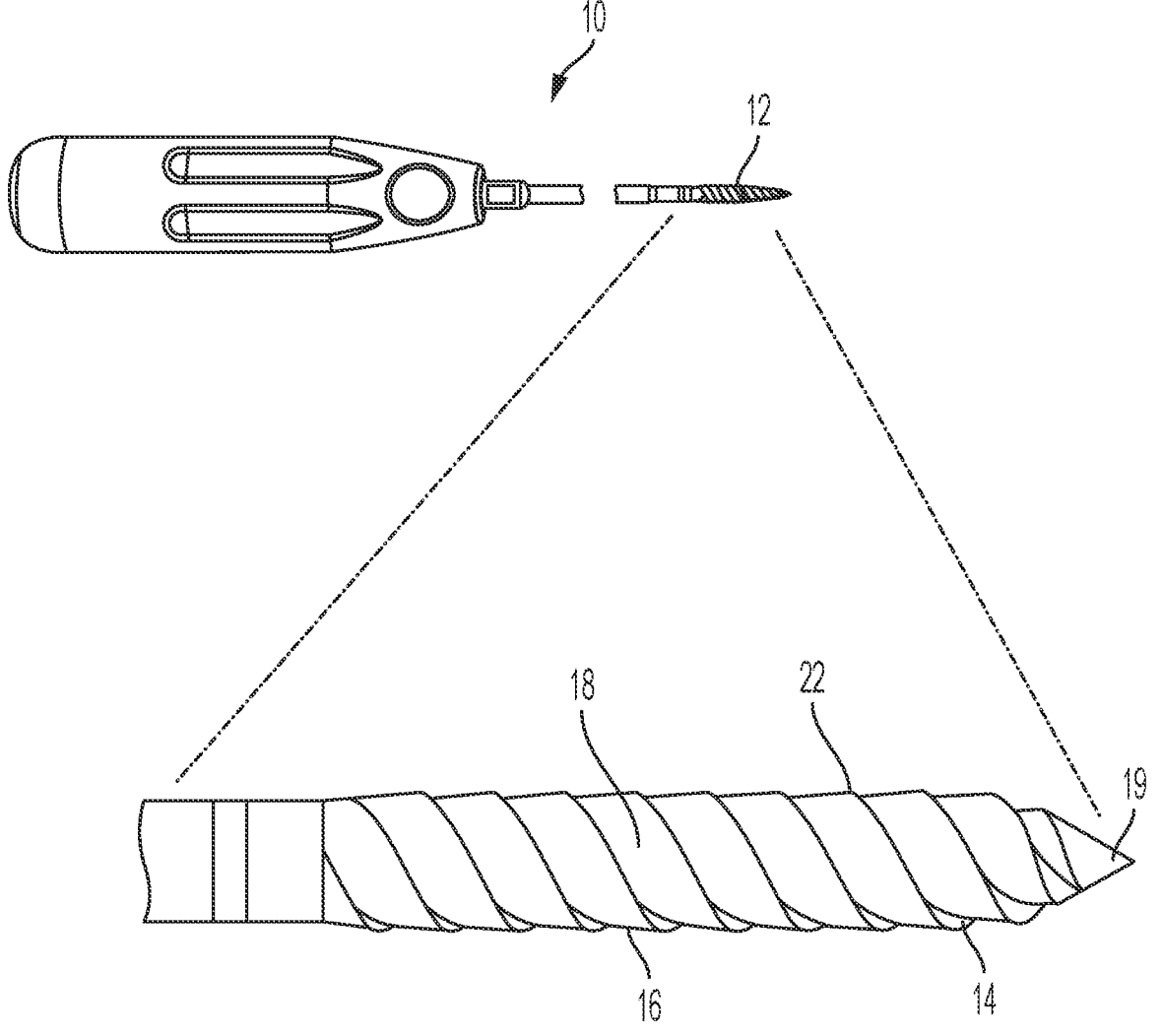
FIG. 1 is a side view of a broaching device including a close up view of a broaching tip having helical broaching features.
Figure 2:
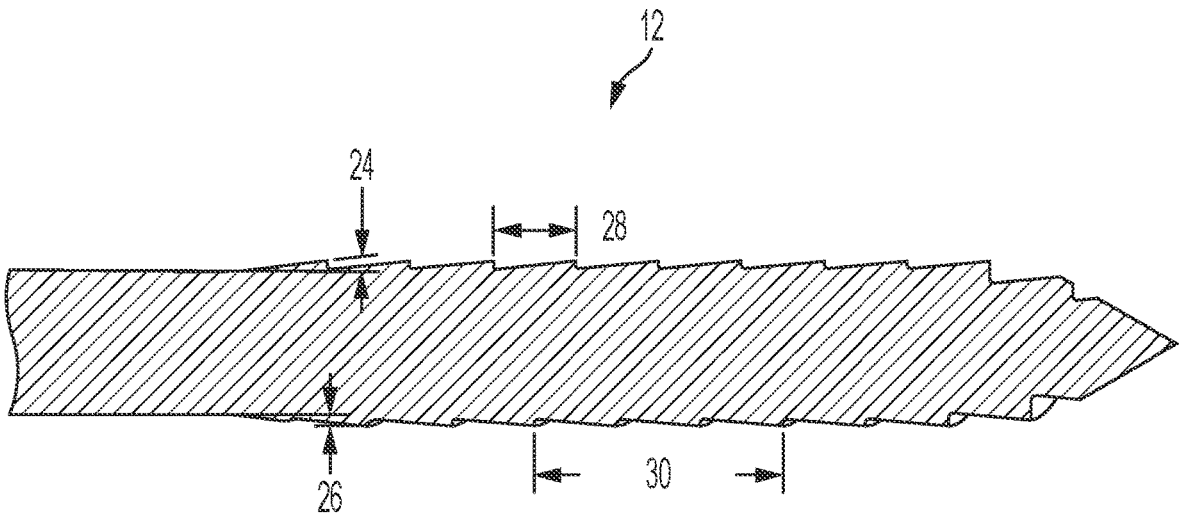
FIG. 2 is a side view of a broaching tip showing the characteristics of the helical edges of the tip.

Referring to the drawings, wherein like numerals refer to like parts throughout, there is seen in FIG. 1 a broaching punch 10 for creating osteotomies. Punch 10 includes a tip 12 having helical broaching features 14 extending along the outer surface 16 of a main body 18 of tip 12 from an intermediate and proximal portion thereof to a distal point 19 of punch 10. As seen in FIG. 2, helical broaching features 14 are formed by a cutting edge 22 extending outwardly from and around body 18 and characterized by a predetermined angle 24, height or depth 26, spacing or pitch 28, and arrangement 30 of various dimensional combinations, as described herein.

Figure 3:
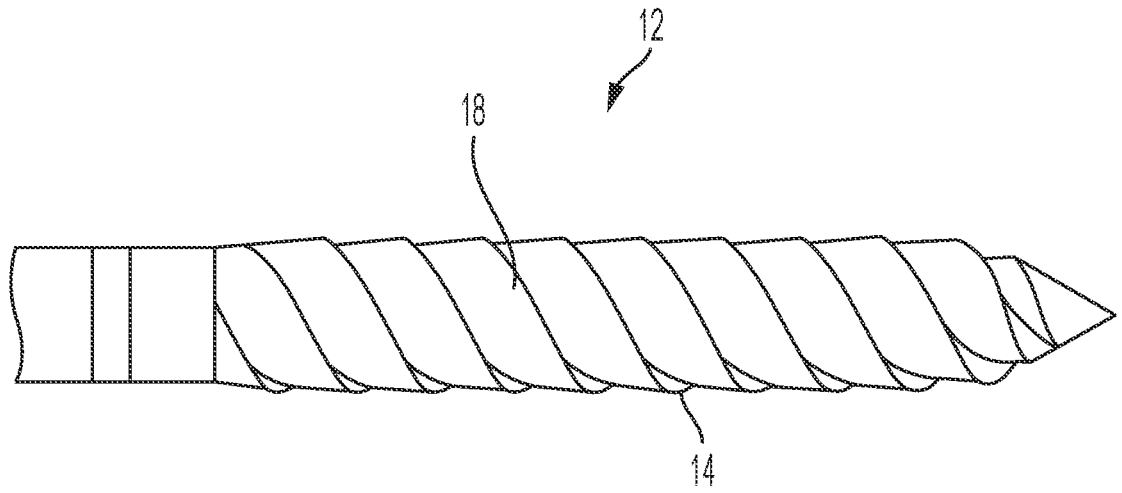
FIG. 3 is a side view of a broaching tip having helical edges that extend in a continuous pitch.
Figure 4:
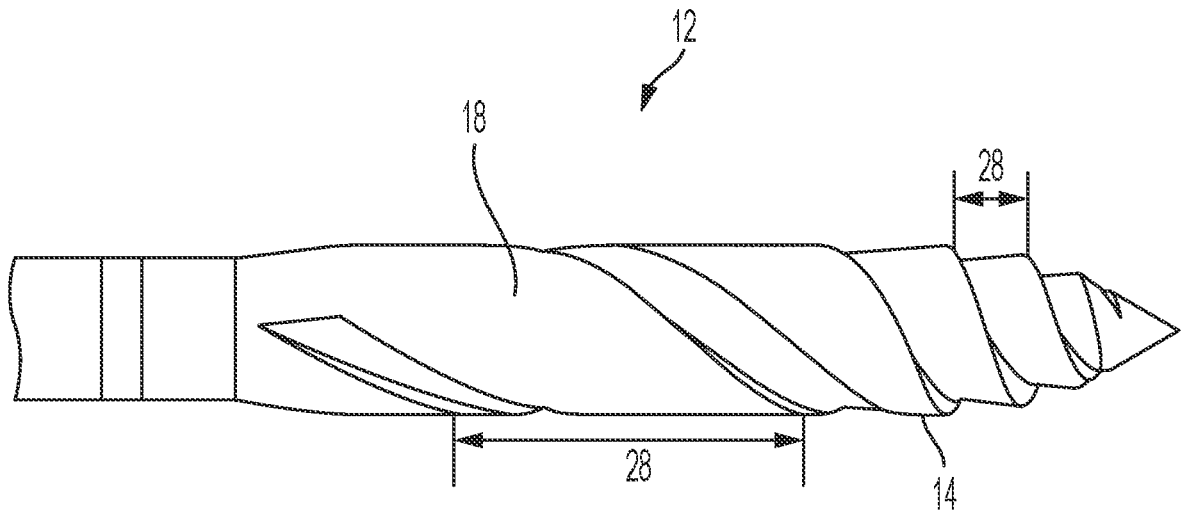
FIG. 4 is a side view of a broaching tip having helical edges that extend in a variable pitch.

The pitch/spacing 28 of helical broaching features 14 can be constant over the length of body portion 18, as seen in FIGS. 2-3 (showing a 3 helix (lead) and a majority constant pitch of, e.g., 0.240", or the pitch/spacing 28 of helical broaching features 14 may be variable, as seen in FIG. 4. An example of an acceptable pitch can be one that allows the punch to be removed with minimal turns while still providing an effective cutting edge for easy insertion. As such, a variable pitch can be preferred in certain circumstances to provide a fast-cutting transition up a taper portion of the tip 12 while still having a fast removal rate by transitioning to a larger pitch as shown in FIGS. 4-5 (as further discussed below with respect to ease of removal in view of particular pitch and number of helixes). The broaching punch tip 12 shown in FIG. 4, for example, has a sharp angled tip with relatively small pitch/spacing 28 (which is a portion of the tip 12 configured to punch and cut into bone until it reaches to the point where the angle as measured from the central longitudinal axis levels off and approaches zero degrees). The angling of the tip 12 then levels off (becomes substantially parallel to the central longitudinal axis at a position proximal to the more sharply angled distal portion) right at or before the pitch/spacing 28 of helical broaching features 14 get relatively longer. The leveling off of the angle and lengthening of the pitches allows for easier and faster removal.

Figure 5A:
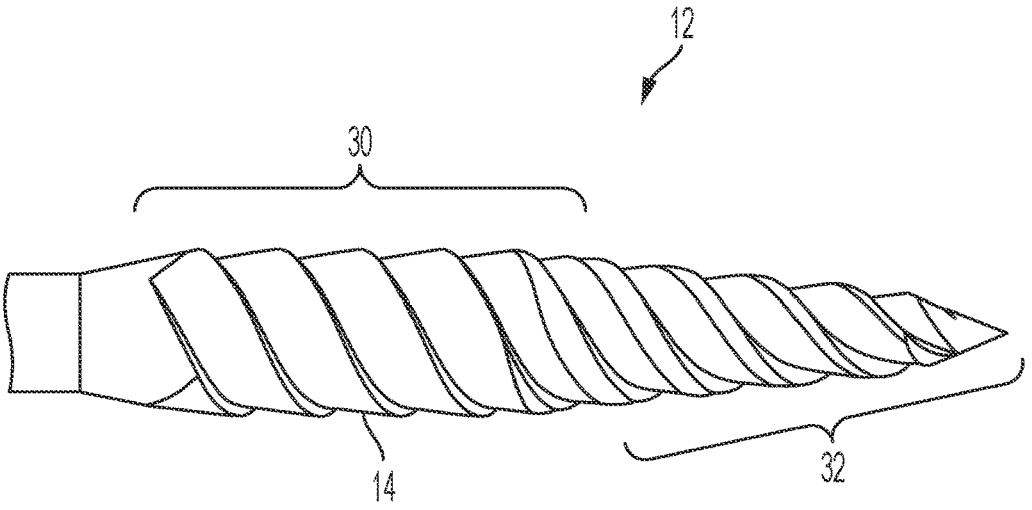
FIG. 5A is a side view of a broaching tip having helical edges that extend cylindrically and in a taper.
Figure 5B:
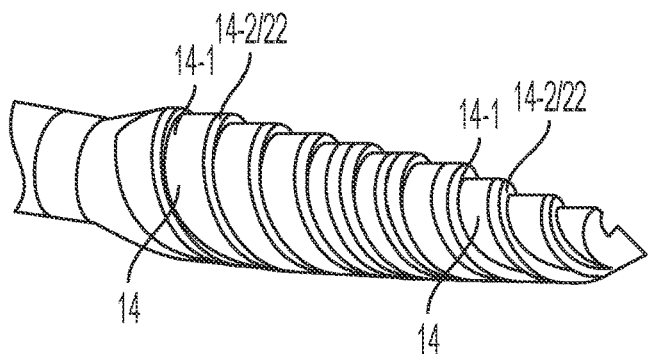
FIG. 5B is a side perspective view of the broaching tip of FIG. 5A.

Referring to FIG. 5A, the external geometry of the outer surface formed by broaching features 14 can have portions or surfaces that are parallel 30, portions or surfaces that are tapered 32, or combinations thereof. Turning to FIG. 5B, a side perspective view of the broaching punch tip 12 of FIG. 5A is shown. Each broaching feature 14 includes a root at the respective proximal edge 14-1, a cutting edge 22 at its respective distal edge 14-2, and a broaching feature body 14 extending therebetween. The cutting edge 22 of each broaching feature 14 extends above (or further away from the central longitudinal axis as compared to) the root/proximal edge 14-1 of its and/or the broaching feature 14 immediately in front of it. Stated differently, in order for the cutting edge 22 to be most effective, it is preferable for the dimensions for angle 24, depth 26 and spacing 28 be configured so that the diameter of cutting edge 22 is larger than the diameter of a proximal edge of the root 14-1 as shown.

As described and illustrated herein, a broaching feature's pitch 28, height or depth 26, and angle 24 (as highlighted in FIG. 2, for example) can be used to define each broaching feature 14 (which may be the same or different from surrounding broaching features 14). These three parameters characterize a triangle and as such, establish a domain of potential values where each parameter can meet a mathematical definition outlined in the following Eq. 1.

$$\text{Tan(angle 24)} = \frac{\text{height 26}}{\text{pitch 28}}$$

An example range of these geometries used for the creation of bone (pilot) holes for the placement and securement of bone anchors, for example, can be 0.025" to 1.3" for broach pitch 28, 0.007" to 0.200" for broach height 26, and 3° to 90° for broach angle 24.

Figure 5C:
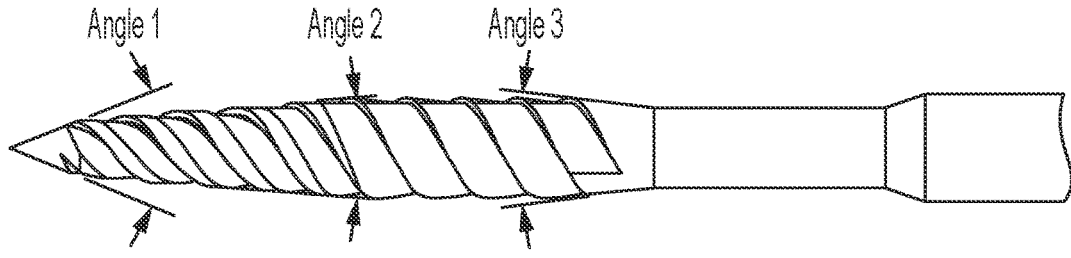
FIG. 5C is an opposite side view of the broaching tip of FIG. 5A.

Additional angles associated with embodiments of the broaching punch 10 can include at least two or more angles associated with the tip 12, as shown in FIG. 5C. Angle 1 is associated with the distal point 19, Angle 2 is associated with the portion of the tip 12 where there is a change in the angle of the tip body after the distal point 19 (moving in the proximal direction along the tip from the distal point 19), and Angle 3 (if there is another angle of the tip 12) is associated with the portion of the tip 12 where there is a change in the angle of the tip body after the portion with Angle 2 (moving in the proximal direction along the tip from the portion of the tip body with Angle 2). The value of Angle 1 can depend on the bone quality and broaching performance required to create a particular pilot hole. For example, in a scenario where the bone is challenging (e.g., dense cortical bone), Angle 1 can have a value from 15° to 45°, Angle 2 can range from greater than 0° to 20° and Angle 3 can be non-existent or range from greater than 0° to 45°. In a scenario where the bone is softer (e.g., cancellous bone), Angle 1 can range from 40° to 180°, Angle 2 can range from −10° to 30°, and Angle 3 can be non-existent or range from greater than 0° to 45°.

Example lengths of tips 12 can be about 1.0 to 2.0", and example diameters to the cutting edge 22 of a broaching feature 14 can range from about 0.01" to 0.50"

Figure 6A:
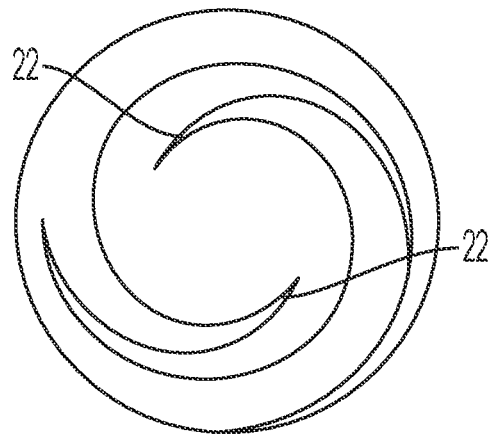
FIG. 6A is an end view of a broaching tip having two edges.
Figure 6B:
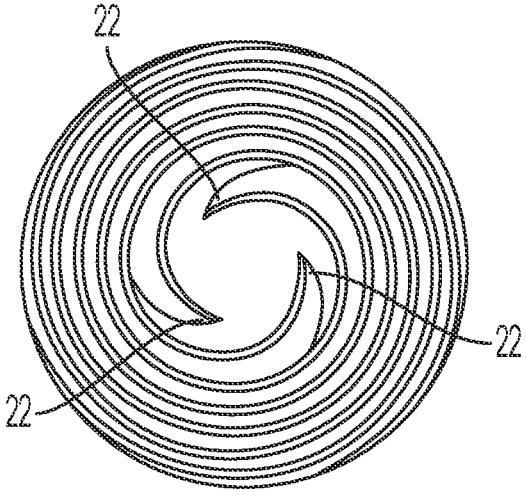
FIG. 6B is an end view of a broaching tip having three edges.
Figure 6C:
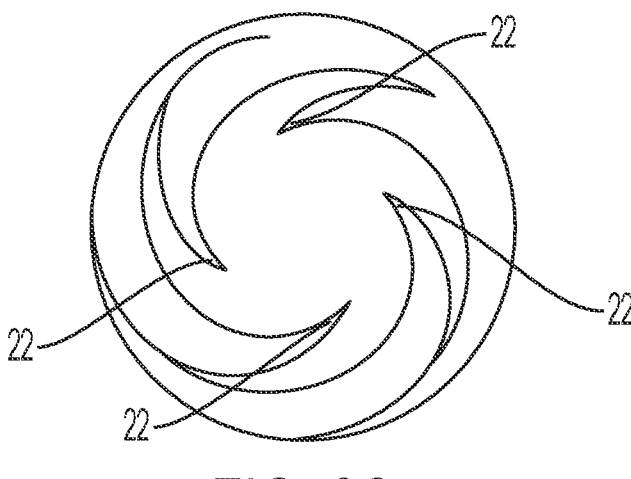
FIG. 6C is an end view of a broaching tip having four edges.

Referring to FIG. 6A through 6C, helical broaching features 14 (which can terminate into a smooth cone with a sharp awl at the distal end) may comprise multiple helixes formed by multiple independent helical edges 22, such as two edges 22 as seen in FIG. 6A, three edges 22 as seen in FIG. 6B, or four edges 22 as seen in FIG. 6C. Using a helical broach allows the broach to be easily removed by unscrewing the broach after axial forced creation of the hole. This is particularly helpful in relatively deep broached holes. To maintain small cuts but allow for faster and easier removal of the broach, additional helixes can be added (as shown FIGS. 6A-C).

Examples of the effect of varying the pitch and number of helixes (which can be tuned based on a number of variables including use/purpose, type of substrate/bone, size of bone, location of bone, etc.) will now be briefly described. A broaching tip with a single helix having a 0.08" pitch would take about 12.5 turns to extract from a 1" deep broached hole. In comparison, a broaching tip with three helixes having a 0.24" pitch would take about 4.1 turns to extract from a 1" deep broached hole. A variable pitched broaching tip example can be used, for example, for harder bone. Such a tip can include a pitch that changes from a small (0.08" pitch) to a larger 0.24" pitch over the distance of desired hole depth. This would provide a relatively gradual change leading up to a desired diameter then a greater pitch to achieve faster removal (see, e.g., FIG. 4).

Figure 7:
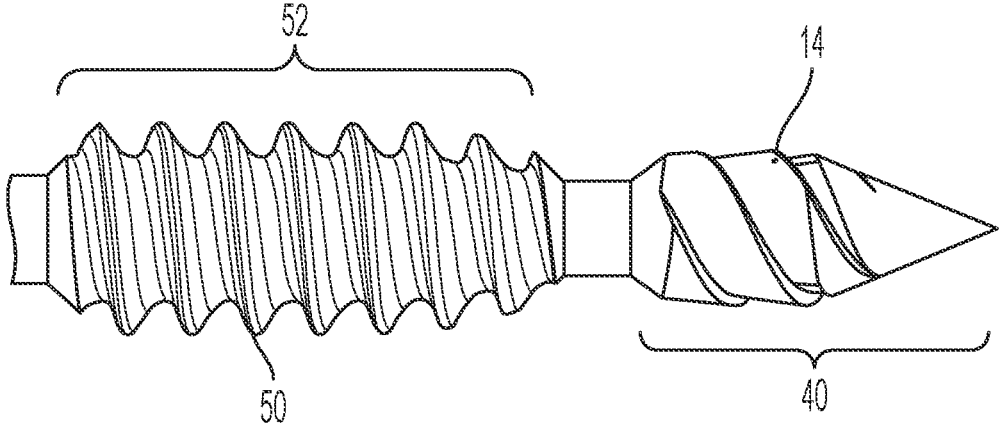
FIG. 7 is a side view of a broaching tip having a threaded portion.

Referring to FIG. 7, another aspect of punch 10 include broaching features 14, as described herein, in a first portion 40 of main body 18 and thread tapping features 50 in a second portion 52 of main body. In this aspect, helical broaching features 14 are used in combination with a tapping feature such that threading can be tapped into an osteotomy as it is created. Conventionally, a tapped osteotomy requires a traditional punch and then a separate tap to create the desired threads in the osteotomy. Using two devices slows down the procedure, as the number of instruments needed is doubled, and the additional time required is especially compounded in situations where several osteotomies are needed to complete a procedure. Additionally, when used arthroscopically, the user must go back down the cannula with the tap to find the pilot hole created by the traditional punch. Often, the surface of the bone is obstructed from view by soft tissue and finding the pilot hole under the scope is difficult. These short comings of conventional devices are avoided by having first portion 40 of main body 18 with broaching features 14 and thread tapping features 50 in a second portion 52 of main body 18 that can be used to form threads in the hole formed by broaching features 14.

In use, broaching punch 10 is driven into predetermined location of the bone so that helical broaching features 14 form an osteotomy. If punch includes tapping features 50, then tapping features 50 may be used to form a tapped osteotomy. The first portion 40 with the broaching features 14 can be punched into bone, and the second portion 52 with the tapping features 50 can be twisted into the bone hole formed by the first portion 40. Users thus only need one device, thereby speeding up the procedure by removing the need to use two devices, relieving the hassle of finding a pilot hole with a tap, and ensuring that any threads also cut into the osteotomy are aligned with the pilot hole. Users will thus cause less damage to patients and greatly reduce the chances of accidental bone fracture. Users will also be able to create more accurate, higher quality osteotomies for medical device insertion and functionality while avoiding any difficulties in removing the device from the patient.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used (e.g., the parameters of the bone hole desired to be formed, and the type of bone in which the bone hole will be formed). Those skilled in the art will recognize, or be able to ascertain using no more than routine experimentation, many equivalents to the specific inventive embodiments described herein (per a review of this disclosure). It is, therefore, to be understood that the foregoing embodiments are presented by way of example only and that, within the scope of the appended claims and equivalents thereto; inventive embodiments may be practiced otherwise than as specifically described and claimed.

Approximating language, as used herein throughout the specification and claims, may be applied to modify any quantitative representation that could permissibly vary without resulting in a change in the basic function to which it is related. Accordingly, a value modified by a term or terms, such as "about" and "substantially" are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein. Further, ranges provide are examples only, and other values are contemplated herein and can depend on potential use of the embodiments described and illustrated herein (as should be understood by a person of ordinary skill in the art in conjunction with a review of this disclosure).

No language in the specification should be construed as indicating any non-claimed element as essential to the practice of the disclosed embodiments.

It will be apparent to those skilled in the art that various modifications and variations can be made to the disclosed embodiments without departing from the spirit and scope of the same. There is no intention to limit the scope of the disclosure to the specific form or forms disclosed, but on the contrary, the intention is to cover all modifications, alternative constructions, and equivalents falling within the spirit and scope of the disclosure.

What is claimed is:

1. A broaching device, comprising:
a tip having a body with an outer surface; and
a plurality of helical broaching features each of which extends continuously around the outer surface of the body and includes a cutting edge positioned on a distal surface thereof and terminating at a distal point, wherein the plurality of broaching features is configured to exert an axial force in the direction of the point.

2. The broaching device of claim 1, wherein the plurality of helical broaching features is selected from the group consisting of two helical broaching features, three helical broaching features, and four helical broaching features.

3. The broaching device of claim 1, wherein the plurality of helical broaching features extend helically around the outer surface of the body in a pitch that is continuous along the body.

4. The broaching device of claim 1, wherein the plurality of helical broaching features extend helically around the outer surface of the body in a pitch that varies along the body.

5. The broaching device of claim 1, wherein the body includes a first portion that extends cylindrically and a second portion that tapers.

6. The broaching device of claim 1, further comprising a set of tapping features positioned adjacently to the plurality of helical broaching features and on an opposite side of the plurality of helical broaching features from the distal point.

* * * * *